United States Patent [19]

Mattiasson et al.

[11] 4,312,944
[45] Jan. 26, 1982

[54] CARRYING OUT ASSAYING METHODS INVOLVING BIOSPECIFIC REACTIONS

[75] Inventors: Bo G. Mattiasson, Trädgårdsmästaren 26, S-222 48 Lund, Sweden; Torbjörn G. I. Ling, Tellusgatan 16, S-223 57 Lund, Sweden

[73] Assignees: Bo Gustav Mattiasson; Torbjörn Gösta Ingvar Ling, both of Lund, Sweden

[21] Appl. No.: 97,176

[22] Filed: Nov. 26, 1979

[30] Foreign Application Priority Data

Nov. 28, 1979 [SE] Sweden ............................... 7812237

[51] Int. Cl.³ ............................................. G01N 33/54
[52] U.S. Cl. ...................................... 435/7; 23/230 B; 424/1; 435/810
[58] Field of Search ................... 23/230 B; 424/1.5, 8, 424/12, 1; 435/4, 7, 810

[56] References Cited

U.S. PATENT DOCUMENTS

| | | | |
|---|---|---|---|
| 3,897,414 | 7/1975 | Albertsson | 536/28 |
| 4,124,700 | 11/1978 | Goldstein | 23/230 B |
| 4,148,869 | 4/1979 | Deaton | 424/8 |
| 4,231,999 | 11/1980 | Carlsson | 424/1 |

OTHER PUBLICATIONS

*Methods of Biochem. Anal.*, vol. 21, 1973, pp. 191–200.
Chemical Abstracts, vol. 80, No. 23, Jun. 1974, 130176z.
Chemical Abstracts, vol. 84, No. 11, Mar. 1976, 71140r.
Albertsson et al., "Counter-Current Dist. of Proteins in Aqueous Polymer Phase Systems", *Nature*, Nov. 7, 1959, pp. 1465–1468.

*Primary Examiner*—Peter A. Hruskoci
*Attorney, Agent, or Firm*—Fred Philpitt

[57] ABSTRACT

An improvement in carrying out assaying methods involving biospecific affinity reactions in which there are used from two to four reactants, one of which reactants, reactant (I), being labelled with at least one analytically indicatable atom or group and being soluble in the aqueous liquid wherein the biospecific affinity reaction is carried out, said reactants forming by biospecific affinity reactions a conjugate in which labelled reactant (I) is incorporated, and in which methods the analytically indicatable atom or group is assayed in the conjugate and/or in the free labelled reactant (I), said improvement being characterized in (a) using as at least one of said reactants a reactant which is modified in such a way that conjugate and free labelled reactant (I) are asymmetrically partitioned in a system of two immiscible aqueous liquid phases, which system in addition to water comprises in dissolved form
  (i) at least two polymers or
  (ii) at least one polymer and at least one salt or
  (iii) at least one polymer and at least one organic solvent,
(b) providing said system of two aqueous liquid phases,
(c) partitioning of conjugate and free labelled reactant (I) in said system of two aqueous liquid phases and
(d) assaying the analytically indicatable atom or group in at least one of the phases.

4 Claims, No Drawings

CARRYING OUT ASSAYING METHODS INVOLVING BIOSPECIFIC REACTIONS

The present invention relates to an improvement in carrying out assaying methods involving biospecific affinity reactions in which there are used from two to four reactants, one of which reactants, reactant (I), being labelled with at least one analytically indicatable atom or group and being soluble in the aqueous liquid wherein the biospecific affinity reaction is carried out, said reactants forming by biospecific affinity reactions a conjugate in which labelled reactant (I) is incorporated, and in which methods the analytically indicatable atom or group is assayed in the conjugate and/or in the free labelled reactant (I).

The term "free labelled reactant (I)" is used in this connection to designate labelled reactant (I) which is not bound to the conjugate.

Immunochemical reactions may be mentioned as an important example of biospecific affinity reactions.

In assaying methods of the aforementioned type involving biospecific affinity reactions (for example immunochemical reactions) a reactant (I) [for example an immunochemical reactant (I)], which is labelled and is soluble in the aqueous liquid wherein the reaction is carried out, is reacted with a reactant (II) which exhibits biospecific affinity to (I) [i.e. (II) is counterpart to (I) and (II) is for example an immunochemical reactant (II)] and optionally also with a third reactant (III) exhibiting biospecific affinity to (I) and/or (II) [i.e. (III) is a counterpart to (I) and/or (II) and (III) is for example an immunochemical reactant (III)] and optionally also with a fourth reactant (IV) exhibiting biospecific affinity to one of the other reactants [i.e. (IV) is a counterpart to one of said other reactants (I), (II) and (III), for example (III), and (IV) is for example an immunochemical reactant (IV)] to the formation of a conjugate (or complex as it also is called) in which labelled reactant (I) is incorporated.

By "immunochemical reactant" is meant in this connection immunoglobulins (including modified immunoglobulins, e.g. aggregated, and fragments, e.g. Fab- or Fc-fragments), preferably antibodies, and antigens and haptens.

Examples of reactants (I) and reactants (II) [as well as reactants (III) and (IV)] which exhibit biospecific affinity to one another [i.e. they are counterparts to each other] are antigens (or haptens) and specific antibodies directed thereagainst. Other examples include (a) Protein A (from S. aureus) and fragments thereof, which can bind the Fc-part of immunoglobulins belonging to the IgG-class; (b) C1g, which can, for example, bind to heat aggregated IgG; (c) lectins (e.g. Concanavalin (A) which, e.g. can bind to specific carbohydrate structures in for example, biopolymers; (d) enzyme inhibitors which can bind to their enzyme; (e) receptors and ligands; (f) physiologically or pharmaceutically active substances capable of binding to corresponding receptors. There are many other such examples of pairs of substances which exhibit biospecific affinity to one another within the biochemical field, e.g. biotin-avidin, intrinsic factor-vitamin B12, etc.

Examples of reactant (III) when such reactant is taking part in the reaction is an unlabelled reactant (I), for instance for competition with labelled reactant (I), or an antibody directed against antibody or antigen in an antigen-antibody-complex in which one of the components is labelled.

Also a fourth reactant (IV) can take part, for instance in the sequence antigen←antibody(A)←antibody(B)←labelled antibody(A).

Many other pairs of reactants of biological origin may be mentioned, the interaction of which is used for assaying methods of the above mentioned type, the concentration of one of the participating reactants being determined.

The statement as to the labelled reactant (I) being soluble in the aqueous liquid in whose presence the biospecific affinity reaction is carried out includes here and in the claims that it, for instance, may be colloidally dispersible in said liquid or in another way be present in the form of particles sufficiently small to keep themselves suspended in the liquid.

A large number of assay methods of the aforementioned basic type, primarily concerning immunochemical assay methods, are known to the art.

In order to enable the assay of the analytically indicatable atom or group in the conjugate or in the labelled reactant (I) which is not bound to the conjugate a partition of said conjugate and said labelled reactant (I) which is not bound to the conjugate is carried out, for instance by means of precipitation methods, chromatographic methods, such as gel filtration, or electrophoretic methods.

An example of such a precipitation method is the socalled double-antibody method in which an insoluble immunochemical conjugate is formed which can be separated from components remaining in the solution.

An example of chromatographic methods is the separation of formed soluble conjugate from free labelled reactant (I), which is not bound to the conjugate, by means of gel permeation chromatography.

In recent years said partition has often been attained by one of the participating reactants [however, not the labelled reactant (I)] being bound to an insoluble polymer so that the conjugate formed by the biospecific reactions will be attached to the insoluble polymer and by reason of that can be separated from free labelled reactant (I) which is not bound to the conjugate but is present in solution. According to one group of such methods, there is used water-insoluble polymer material to which is bound an antibody or an antigen, for example a polypeptide-containing antigen or some other counterpart. Thus, it is known from, for example, British Patent Specification Nos. 1,192,784, 1,248,764 and 1,248,765 and Biochem. Biophys. Acta 130 (1966) page 257, and Radio-immunoassay Methods (Editors: K. E. Kirkham and W. M. Hunter, Churchil Livingstone, London 1971) e.g. pages 405-412 of the article "Solid Phase Antigen Antibody Systems" by L Wide, to use a water-insoluble polymer material to which an antibody or an antigen is bound by bonds of a covalent nature. Further, the U.S. Pat. No. 3,646,346 teaches an immunochemical assay method in which there is used antibodies adsorbed on the inner surface of a plastics test tube.

It is also known, when carrying out the immunochemical and analogous assay methods in question, that one of the reactants [reactant (I)] involved in the assay method is labelled with an analytically indicatable atom or group, e.g. with a radioactive atom or group, a fluorescent, luminescent or chromophoric group, or an enzymatically active group or an enzyme inhibitor group or a coenzyme group.

The labelling of the reactant (I) (e.g. an antigen, an antibody etc.) with an analytically indicatable atom or group is nowadays wellknown and well established techniques for this are generally known. In this connection it is known that the label can be directly bound to the reactant (I) or that a bridge is introduced between the reactant (I) and the label.

A large number of variants of such assay methods (including immunochemical assay methods as well as analogous assay methods utilizing other reactants than immunochemical reactants which reactants have biospecific affinity to each other) in which there is used a labelled reactant, for example a labelled antigen, a labelled hapten, a labelled antibody or labelled protein A are known and described in the literature. (See for example the aforementioned references). Thus, for example (a) antibodies can be reacted with an antigen in a sample and with labelled antigen or (b) antibodies can be reacted with an antigen in a sample in a manner such that the antigen is bound to the antibody, whereafter there is added labelled antibodies which bind to the bound antigen, or (c) an antigen is reacted with an antibody in a sample in a manner such that the antibody binds to the antigen, whereafter there is added labelled antigen which bind to the bound antibody, or (d) an antigen is reacted with an antibody in a sample in a manner such that the antibody binds to the antigen, whereafter there are added labelled antibodies directed against the first-mentioned antibodies and binding thereto, (e) an antigen in a sample is reacted with a labelled antibody, (f) an antibody in a sample is reacted with a labelled hapten or antigen.

The antibodies may belong to one or more immunoglobulin classes. What has been said concerning assay methods involving antigens and antibodies also applies to analogous assay methods involving other reactants than antigens and antibodies.

It is also well known that such assays are preferably carried out in the presence of an aqueous liquid, e.g. a buffer solution having a suitable pH and ion strength.

In case of the quantitative assay of one of the reactants it is also well known to use varying known amounts of this reactant in order to establish standard curves which are then used for the determination of unknown amounts of said reactant.

A common disadvantage of all the above prior art methods is the laborous and time-consuming partitioning and separation of the conjugate and free labelled reactant (I). For instance in precipitation methods and methods using an insoluble polymer the material of the solid phase (i.e. the precipitate and the insoluble material with substances attached thereto, respectively) is usually separated from the liquid phase by repeated centrifugation and washing procedures.

Accordingly, it is an object of the present invention to provide a method wherein partition of the conjugate and free labelled reactant (I) is effected rapidly and simply without affecting the accuracy of the method to any substantial degree. Another object of the present invention is to provide a method in which non-specific adsorption of labelled reactant (I) to an insoluble polymer (i.e. used for separation) can be avoided, particularly when the label is an enzymatically active group. Thus, the invention extends the possibility to use enzymes as labels in this type of assaying methods.

These and other objects are achieved according to the present invention by means of a method of the type set forth in the introductory part of this specification, which method is characterized in (a) using as at least one of said reactants a reactant which is modified in such a way that conjugate and free labelled reactant (I) are asymmetrically partitioned in a system of two immiscible aqueous liquid phases, which system in addition to water comprises in dissolved form
 (i) at least two polymers or
 (ii) at least one polymer and at least one salt or
 (iii) at least one polymer and at least one organic solvent,
(b) providing said system of two aqueous liquid phases,
(c) partitioning of conjugate and free labelled reactant (I) in said system of two aqueous liquid phases and
(d) assaying the analytically indicatable atom or group in at least one of the phases.

The present invention is based on the principle that biological molecules, especially macromolecules, having considerably different surface structures may be partitioned asymmetrically in systems of two aqueous liquid phases. The asymmetrical partitioning is due to differences in physical affinity of the molecules to at least one of the two phases. For instance, one substance may be dissolved to a greater extent in the lower phase than in the upper phase of the two phase system whereas another substance may be dissolved to a greater extent in the upper phase or the two substances may be dissolved to a greater degree in one of the phases than in the other phase but to different degrees when compared to each other. For the purpose of the present invention, however, the modification of reactant(s) is preferably performed in such a way that the conjugate is predominantly partitioned to one of the two phases and the free labelled reactant (I) is predominantly partitioned to the other phase.

In accordance with one aspect of the present invention the modification of at least one of the reactants may be effected by coupling to the surface of the reactant molecule or molecules to be modified one or more substituent groups which change the surface structure of the molecule or molecules in a direction of increased hydrophobicity or hydrophilicity. The substituents may be coupled to the reactant via for example carbon-nitrogen, carbon-oxygen, carbon-carbon or sulphur-sulphur linkages, e.g. over amide, ether, ester or carbamic acid ester bridges in a manner known per se, An ether bridge may, for instance, be established by reacting a reactant to be modified containing at least one hydroxyl group with an epoxy derivative of the substituent, for instance a substance containing the radical

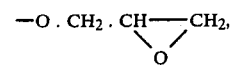

or the corresponding halohydrin.

A hydroxyl group containing reactant to be modified may also be reacted with an alcohol and a bifunctional bridge-forming agent of the formula $X_1.A_1.Z$, wherein X and Z each represents a halogen atom, preferably chlorine or bromine, and $A_1$ is a straight or branched, aliphatic saturated hydrocarbon chain which is substituted by one or more hydroxyl groups and preferably contains 3-10 carbon atoms and possibly is broken by one or more oxygen atoms, or the corresponding epoxy compounds obtainable by splitting off hydrogen halide. The alcohol may be an aliphatic or aromatic alcohol.

In order to obtain an ester- or amide-bound substituent a compound of, for instance, the formula $R.CO.X_2$ wherein R is the substituent to be introduced and $X_2$ is a chlorine or bromine atom, or the corresponding acid anhydride is reacted with a reactant to be modified which contains at least one hydroxyl or amino group.

Other ways of introducing the substituent groups are, for instance, to react amino groups or hydroxyl groups in the reactant to be modified with a chloro-s-triazine derivative of the substituent, for example a chloro-s-triazine derivative of a polymer, such as for example a polyethylene glycol or a water soluble polysaccharide.

Reactants to be modified containing amino groups can also be reacted with an epoxy (or the corresponding halo hydrin) derivative of the substituent.

Reactants to be modified containing carboxyl groups, may be reacted with a compound containing the substituent and a hydroxyl or amino group. In this connection carbodiimides may be used to facilitate the formation of ester or amide bridges.

Suitable substituents for increasing the hydrophobicity are for instance hydrophobic low molecular weight (small) substituents such as lower hydrocarbon residues and hydrophobic high molecular weight (big) substituents such as more or less hydrophobic macromolecules such as polyethylene glycol or polypropylene glycol residues. The desired degree of hydrophobicity may be achieved by using a great number of small substituents or a low number of big substituents.

Suitable substituents for increasing the hydrophilicity are for instance substituents containing ionizable groups (such as substituents containing carboxyl, sulfonic, amino) and hydroxyl groups. (The amino groups may be primary, secondary, tertiary or quarternary amino groups.) The hydrophilic substituents may be of a low molecular weight structure or of a high molecular weight structure such as polysaccharides, for instance dextran.

The desired degree of hydrophilicity may be achieved by using a great number of small substituents or a low number of big substituents.

The biospecific affinity of the reactant shall of course not be destroyed by the modification.

Preferably polymeric hydrophobic or hydrophilic substituents are used for the modification whereby a low degree of substitution can be chosen.

When a macromolecular substituent is used it may be to advantage to use a substituent which is derived from a water-soluble polymer which is used for the formation of the aqueous liquid phase system.

In accordance with another aspect of the present invention the aqueous two phase system of liquids may be a system known per se for the fractionation of mixtures of e.g. high molecular weight substances of different physical characteristics by means of two immiscible aqueous and (usually) polymeric liquids (top phase and bottom phase liquid). A great number of such systems is described for instance in Albertsson, P-Å, "Partition of Cell Particles and Macromolecules", Uppsala, 1st edition 1960 and 2nd edition 1971 and U.S. Pat. No. 3,897,414 (Albertsson). Examples of such two phase systems of aqueous and polymer containing liquids are: Dextran/water-soluble copolymer of sucrose and epichlorohydrin (Ficoll)/water, dextran/hydroxypropyldextran/water, polyethylene glycol/dextran sulphate/water, charged polyethylene glycol/dextran/water, dextran/polyethylene glycol/water, polypropylene glycol/methoxypolyethylene glycol/water, polypropylene glycol/polyethylene glycol/water, polypropylene glycol/polyvinyl alcohol/water, polypropylene glycol/polyvinyl pyrrolidone/water, polypropylene glycol/hydroxypropyldextran/water, polypropylene glycol/dextran/water, polyethylene glycol/polyvinyl alcohol/water, polyethylene glycol/polyvinyl pyrrolidone/water, polyethylene glycol/Ficoll/water, polyethylene glycol/soluble starch/water, polyethylene glycol/glycogen/water, polyvinyl alcohol/methyl cellulose/water, polyvinyl alcohol/hydroxypropyl dextran/water, polyvinyl alcohol/dextran/water, polyvinyl pyrrolidone/methyl cellulose/water, polyvinyl pyrrolidone/dextran/water, methyl cellulose/hydroxypropyl dextran/water, methyl cellulose/dextran/water and ethylhydroxyethyl cellulose/dextran/water. Such aqueous two phase systems containing at least two water-soluble polymers may also contain an addition of salt or organic solvent.

Other groups of aqueous two phase liquid systems which may be used in accordance with the present invention are at least one polymer/at least one salt/water and at least one polymer/at least one organic solvent/water. Examples of water-soluble polymers have been given above. The polymer may for example be polyethylene glycol, polypropylene glycol, polyvinylpyrrolidone or a polysaccharide, or water-soluble derivative thereof. The salt may be an inorganic salt or an organic salt which is soluble in water, for example a sulphate, a phosphate or a chloride, e.g. magnesium sulphate, potassium phosphate or sodium chloride. The organic liquid should be a water-soluble organic solvent which does not affect the properties of any of the reactants taking part in the biospecific affinity reactions. Examples of organic solvents which may be used in an aqueous two phase system according to the present invention are propylalcohol, glycerol and 2-butoxyethanol.

The invention will be further illustrated by means of a number of specific examples. (In the examples the solutions are aqueous solutions unless otherwise stated.)

EXAMPLE 1

Quantitative determination of IgE in serum using a competitive radioimmuno assay method A. 5.5 g (0.03 mole) of cyanuric chloride were dissolved in 400 ml of anhydrous benzene containing 10 g of anhydrous sodium carbonate. 20 g (0.01 mole) of monomethyl ether of polyethylene glycol of 2000 daltons (methoxy-PEG-2000) (from Union Carbide Chemicals, New York, U.S.A.) were added and the mixture was stirred over night at room temperature. The solution was filtered, and 600 ml of petroleum ether (boiling range 60°–71° C.) was added slowly with stirring. The precipitate was collected on a filter and redissolved in 400 ml of benzene. The precipitation and filtration process was repeated five times. The product thus obtained, 2-O-methoxypolyethylene glycol-4,6-dichloro-s-triazine, will in the following be called "activated methoxy-PEG-2000".

B. 2 mg of antibodies against the Fc-part of IgE (anti-$D_2$) (prepared according to Example 2 of British Patent Specification No. 1,248,764) were incubated with 50 mg of activated methoxy-PEG-2000 in 1 ml 0.1 M triethanolamine buffer pH 9.3 over night. (Hydrolysis of the second chlorine of cyanuric chloride occurs readily under conditions used for coupling the activated PEG-derivate to protein; consequently a considerable excess of said derivative must be used in the coupling reaction.)

C. IgE standard serum was obtained by diluting a patient serum with horse serum to the following concentrations: 4000, 400, 100, 50, 25, 10 and 2 International Units (I.U.) IgE/ml.

D. 100 μl IgE standard and 100 μl $^{125}$I-labelled IgE (69844 cpm) (from Phadebas® RIST-IgE kit from Pharmacia Diagnostics AB, Uppsala, Sweden) were mixed with 100 μl of modified anti IgE diluted with 0.1 M sodium phosphate buffer, pH 7.4 to a concentration of 10 μg/ml. This mixture was incubated over night at room temperature on a shaking table. Then 4 ml of an aqueous phase mixture obtained by mixing 3 ml of 30% (w/v) MgSO$_4$.7H$_2$O and 1 ml 30% (w/v) polyethylene glycol of 4000 daltons were added. After 5 minutes a sample of 0.5 ml of the top phase (the polyethylene glycol-rich phase) could be taken out for analysis in a γ-counter.

The following results were obtained:

| IgE in international units | Counts per minute |
| --- | --- |
| 4000 | 1600 |
| 400 | 3300 |
| 100 | 7200 |
| 50 | 9000 |
| 25 | 10500 |
| 10 | 11700 |
| 2 | 13800 |
| 0 | 14100 |

The counts per time unit were plotted against the logarithm of the concentration of IgE in the samples.

Thus a standard curve was obtained which then was used for the determination of unknown concentration of IgE in test samples.

EXAMPLE 2

Quantitative determination of specific IgE in serum using a sandwich radioimmuno assay method A. 2 mg of dog albumin (from Sigma Chemical Company, Saint Louis, U.S.A.) were incubated with 50 mg of activated methoxy-PEG-2000 (prepared as in Example 1, section A, in 1 ml of 0.1 M triethanolamine buffer pH 9.3 over night.

B. Patient serum with IgE specific against dog albumin (from Pharmacia Diagnostics AB, Uppsala, Sweden) was diluted with serum free from IgE to different IgE-concentrations down to ⅛ of the original serum. 100 μl of each dilution were then mixed with 100 μl of modified dog albumin (diluted to 20 μg/ml with 0.1 M sodium phosphate buffer, pH 7.4) and incubated for 3 h at room temperature on a shaking table. Then 4 ml of a phase mixture comprising 3 ml 30% (w/v) MgSO$_4$.7H$_2$O in water and 1 ml of 30% (w/v) polyethylene glycol of 4000 daltons were added. After 5 minutes a sample of 0.5 ml of the top phase (i.e. the phase rich in polyethylene glycol) was taken for incubation on a shaking table with 100 μl $^{125}$I-labelled anti IgE (ca. 55000 cpm) (from Phadebas® RAST-kit from Pharmacia Diagnostics AB, Uppsala, Sweden) over night. Then the above mentioned phase mixture was added once more and another separation was allowed to take place. Finally the radiation from 200 μl of the top phase was measured in a γ-counter.

The counts per time unit were plotted against the logarithm of the concentration of IgE specific against dog albumin. Thus a standard curve was obtained which then was used for the determination of unknown concentrations of IgE specific against dog albumin in test samples.

EXAMPLE 3

Quantitative determination of specific IgE in serum using a sandwich enzyme immuno assay method The same procedure as in Example 2 was used but 100 μl of β-galactosidase-labelled anti IgE (360 ng/ml) (prepared by using a procedure analogous to the one described in German "Offenlegungsschrift" No. 2 808 515 /Example 8a/ for the coupling of β-galactosidase to antibodies) in 0.1 M sodium phosphate, pH 7.4 were added instead of $^{125}$I-labelled anti IgE and 200 μl of the upper phase were analysed for galactosidase activity using 1 ml of a substrate having the following composition:

16.5 mg o-nitrophenyl β-galactoside
10 mg MgCl$_2$
50 ml 0.1 M sodium phosphate buffer pH 7.0.

The enzyme activity was measured for each concentration after 120 minutes by determining the absorbance at 405 nm and the values were plotted against the different concentrations of IgE specific against dog albumin in a diagram.

Thus a standard curve was obtained which then could be used for the determination of unknown concentrations of IgE specific against dog albumin in the same way as in Example 2.

EXAMPLE 4

Quantitative determination of glucose

A. Using the procedure described in Example 1, section A, monomethyl ether of polyethylene glycol of 5000 daltons (methoxy-PEG-5000) (from Union Carbide Chemicals, New York, U.S.A.) was reacted with cyanuric chloride using a 1:3 molar ratio of said monomethyl ether to cyanuric chloride. The product thus obtained will in the following be called "activated methoxy-PEG-5000".

Concanavalin A was dissolved in 0.1 M triethanolamine, 0.1 M NaCl, pH 9.4 and activated methoxy-PEG-5000 was added to a concentration of 9.2 mg Concanavalin A and 10 mg activated metoxy-PEG-5000 per ml triethanolamine buffer. The mixture was stirred for 1 h at room temperature. Unattached activated methoxy-PEG-5000 was removed by dialysis against 0.5 M NaCl, 0.1 M Na-phosphate, pH 7.00 (PBS).

C. 8 nmole of C-14-glucose, 20 nmole of methoxy-PEG-5000-Concanavalin A and varying amounts of glucose were dissolved in PBS to a total volume of 200 μl. The mixture was stirred on a vortex-type mixer and left 30 minutes at room temperature. Then the reaction mixture was subjected to partitioning in a polymeric aqueous two phase system obtained by mixing 900 μl 30% (w/w) polyethylene glycol of 4000 daltons, 900 μl 30% (w/w) MgSO$_4$.7H$_2$O. The tubes were shaken thoroughly and the phases were allowed to separate for 10 minutes. Then 200 μl of the top phase were transferred to scintillation vial and the radioactivity determined.

The following results were obtained:

| Glucose (mM) | Radioactivity in the top phase (counts per minute) |
| --- | --- |
| 0 | 2126 |
| 0.5 | 2047 |
| 0.7 | 2002 |
| 1.0 | 1803 |
| 2.0 | 1682 |
| 5.0 | 1520 |
| 7.0 | 1440 |
| 10.0 | 1390 |

A standard curve could be obtained on the basis of these values which standard curve could then be used for the determination of unknown concentration of glucose in test samples.

EXAMPLE 5

Biotin assay using competitive binding to avidin

A. 0.1 mmole of 1-ethyl-3-(3-dimethylaminopropyl)-carbodiimide hydrochloride (EDC) (from Sigma Chemical Company, St. Louis, U.S.A.) and 0.1 mmole of N-hydroxysuccinimide were dissolved in 1 ml of a mixture of dioxane and water (volume ratio 1:1). 0.01 mmole of biotin (from Sigma Chemical Company, St. Louis, U.S.A.) was added and the mixture was stirred for 1 h at room temperature.

B. 35 nmole of activated biotin thus obtained was added to 1.5 ml of a solution containing horse radish peroxidase (7 nmole) (from Sigma Chemical Company, St. Louis, U.S.A.) in distilled water. The reaction was allowed to continue for 15 minutes at 4° C. The conjugated protein thus obtained was dialysed against PBS overnight.

C. Using the procedure described in Example 4, section B, 7.0 mg of avidin were reacted with 10 mg of activated methoxy-PEG-5000 in 1 ml 0.1 M triethanolamine buffer, 0.1 M NaCl, pH 9.4.

D. 0.90 nmole of methoxy-PEG-5000-derivatized avidin (from C. above), 0.48 nmole of biotinylperoxidase (from B. above) and varying concentrations of biotin (dissolved in PBS of volumes less than 120 $\mu$l) were dissolved in PBS to a total volume of 240 $\mu$l. The mixture was stirred and then left for 10 minutes. Then the following phase system components and assay reagents for quantification of enzyme activity in the bottom phase were added:

1800 $\mu$l 30% (w/w) MgSO$_4$.7H$_2$O
1800 $\mu$l 30% (w/w) polyethylene glycol of 4000 daltons
80 $\mu$l 700 mM phenol
80 $\mu$l 40 mM 4-aminoantipyrine
80 $\mu$l 50 mM hydrogen peroxide.

After phase separation (approx. 4 minutes) the amount of enzyme in the bottom phase was determined photometrically. (The separation and the subsequent assay may be performed in the same cuvette if a photometer is used that can measure in the bottom phase in the cuvette only.) The following results were obtained:

| Biotin added (pmole) | Reactivation of the enzyme* (%) |
| --- | --- |
| 30 | 23 |
| 60 | 32 |
| 120 | 45 |
| 180 | 51 |
| 240 | 58 |
| 300 | 61 |
| 360 | 64 |
| 480 | 71 |
| 600 | 76 |

*As a reference value is used the enzymatic activity with no avidin present. When PEG-derivatized avidin is added, the enzyme activity decreases, and when free biotin is added an increase in enzyme activity in the bottom phase is observed. This is above called reactivation.

The values obtained may be used in a calibration curve for quantification of unknown concentrations of biotin in samples.

EXAMPLE 6

Avidin assay 0.90 nmole of methoxy-PEG-5000-derivatized avidin (from Example 5, section C.), 0.48 nmole of biotinylperoxidase (from Example 5, section B.) and varying concentrations of avidin were dissolved in PBS to a total volume of 240 $\mu$l. The reagents were mixed and then left for 10 minutes. Then the same phase system and assay reagents for quantification of the enzyme activity in the bottom phase as in Example 5 were added.

After phase separation (approx. 4 minutes) the enzyme activity was assayed in the bottom phase according to the procedure described in Example 5.

The following results were obtained:

| Avidin concentration ($\mu$M) | Reactivation of the enzyme* (%) |
| --- | --- |
| 2 | 0 |
| 10 | 13 |
| 20 | 21 |
| 40 | 31 |
| 60 | 47 |
| 80 | 66 |
| 100 | 71 |
| 120 | 73 |

*For definition, vide Example 5.

We claim:

1. The improvement in carrying out, in the presence of an aqueous liquid, assaying methods involving biospecific affinity reactions in which there are used from two to four reactants, one of which reactants, reactant (I), being labelled with at least one analytically indicatable atom or group and being soluble in the aqueous liquid wherein the biospecific affinity reaction is carried out, said reactants forming by biospecific affinity reactions a conjugate in which labelled reactant (I) is incorporated, and in which methods the analytically indicatable atom or group is assayed in at least one member of the group comprising the conjugate and the labelled reactant (I), which is not bound to the conjugate, which comprises (a) using as at least one of said reactants a reactant which is modified in such a way that conjugate and labelled reactant (I), which is not bound to the conjugate, are asymmetrically partitioned in a system of two immiscible aqueous liquid phases, due to differences in physical affinity of the molecules to at least one of the two phases, which system in addition to water comprises in dissolved form, (i) at least two water-soluble polymers, or (ii) at least one water-soluble polymer at at least one water-soluble salt, or
(iii) at least one water-soluble polymer and at least one water-soluble organic solvent,
(b) providing said system of two aqueous liquid phases,
(c) partitioning of conjugate and labelled reactant (I) which is not bound to the conjugate, in said system of two aqueous liquid phases by the addition thereof to said system and allowing the phases to separate, and (d) assaying the analytically indicatable atom or group in at least one of the phases.

2. A method according to claim 1 wherein the modified reactant used contains a substituent which is derived from a soluble polymer which is used for the formation of the aqueous liquid phase system.

3. A method according to claim 2 wherein said soluble polymer is polyethylene glycol.

4. A method according to claim 1 or 2 or 3 wherein the analytically indicatable group is an enzymatically active group.

* * * * *